United States Patent

Faupel et al.

[11] Patent Number: 5,823,957
[45] Date of Patent: *Oct. 20, 1998

[54] D.C. BIOPOTENTIAL SENSING ELECTRODE AND ELECTROCONDUCTIVE MEDIUM FOR USE THEREIN

[75] Inventors: Mark L. Faupel, Conyers; Burke T. Barrett, Roswell; John D. Stephens; Seth D. Nathanson, both of Alpharetta, all of Ga.

[73] Assignee: Biofield Corp, Roswell, Ga.

[*] Notice: The term of this patent shall not extend beyond the expiration date of Pat. No. 5,660,177.

[21] Appl. No.: 508,206

[22] Filed: Jul. 27, 1995

Related U.S. Application Data

[63] Continuation-in-part of Ser. No. 325,085, Oct. 17, 1994, Pat. No. 5,660,177.

[51] Int. Cl.⁶ .................................................. A61B 5/0408
[52] U.S. Cl. .......................... 600/397; 600/392; 600/396; 252/518.1
[58] Field of Search ..................................... 128/639–641, 128/644; 607/153; 252/500, 518, 519, 518.1, 519.1; 600/372, 386, 395–397, 391, 392

[56] References Cited

U.S. PATENT DOCUMENTS

| | | |
|---|---|---|
| Re. 31,454 | 12/1983 | Hymes . |
| 3,027,333 | 3/1962 | Friedman . |
| 3,567,657 | 3/1971 | Lichtenstein . |
| 3,828,766 | 8/1974 | Krasnow . |
| 3,868,946 | 3/1975 | Hurley . |
| 3,964,469 | 6/1976 | Manley . |
| 3,976,055 | 8/1976 | Monter et al. . |
| 3,989,035 | 11/1976 | Zuehlsdorff . |
| 4,034,854 | 7/1977 | Bevilacqua . |
| 4,114,263 | 9/1978 | Szpur . |
| 4,126,126 | 11/1978 | Bare et al. . |
| 4,166,453 | 9/1979 | McClelland . |
| 4,282,878 | 8/1981 | Novello . |
| 4,317,278 | 3/1982 | Carmon et al. . |
| 4,362,165 | 12/1982 | Carmon et al. . |
| 4,365,634 | 12/1982 | Bare et al. . |
| 4,406,872 | 9/1983 | Carim ....................................... 128/639 |
| 4,570,637 | 2/1986 | Gomes et al. . |
| 4,583,549 | 4/1986 | Manoli . |
| 4,617,935 | 10/1986 | Cartmell ................................... 128/641 |
| 4,692,273 | 9/1987 | Lawrence ................................. 128/640 |
| 4,742,828 | 5/1988 | Sundstrom . |
| 4,763,660 | 8/1988 | Kroll et al. . |
| 4,787,390 | 11/1988 | Takata . |
| 4,957,109 | 9/1990 | Groeger et al. . |
| 5,042,481 | 8/1991 | Suzuki et al. . |
| 5,660,117 | 8/1997 | Faupel et al. ............................ 128/639 |

OTHER PUBLICATIONS

"American National Standard for Pregelled ECG Disposable Electrodes", Association for the Advancement of Medical Instrumentation, 1984.

*Primary Examiner*—Lee S. Cohen
*Attorney, Agent, or Firm*—Sixbey, Friedman, Leedom & Ferguson; Daniel W. Sixbey

[57] ABSTRACT

A DC biopotential sensing electrode assembly is provided for an apparatus for sensing DC biopotentials present at the skin of a subject. An electroconductive medium for transmitting ions from the skin which has a chloride ion content within a range of from 6–15 grams per hundred grams of such medium is formulated for use with the electrode. To reduce the corrosive effect of this electroconductive medium, each electrode includes only one metallic component, and to provide an electrode with a low AC impedance, this metal is uniformly coated upon nonmetallic sensor and terminal bodies with a coating thickness within a range of from 0.5 to 1.5 mil. To insure a complete electrical path through both the sensor and the terminal bodies, the nonmetallic portions are formed of conductive plastic.

38 Claims, 4 Drawing Sheets

D.C. BIOPOTENTIAL SENSING ELECTRODE AND ELECTROCONDUCTIVE MEDIUM FOR USE THEREIN

This application is a continuation-in-part application of Ser. No. 08/325,085 filed Oct. 17, 1994 U.S. Pat. No. 5,660,177.

TECHNICAL FIELD

The present invention relates generally to an apparatus for screening or sensing disease states, injury sites or bodily conditions in a living organism by detecting the DC biopotential of the electromagnetic field present between a reference and a plurality of test points on the living organism to measure the gradient of electrical activity which occurs as a function of biological activity, and more particularly to DC biopotential sensing electrodes for use with such apparatus and an electroconductive medium with a high chloride ion content for use in such electrodes.

BACKGROUND ART

In recent years the theory that measurement of the potential level of the electromagnetic field of a living organism can be used as an accurate screening and diagnostic tool is gaining greater acceptance. Many methods and devices have been developed in an attempt to implement this theory. For example, U.S. Pat. No. 4,328,809 to B. H. Hirschowitz et al. deals with a device and method for detecting the potential level of the electromagnetic field present between a reference point and a test point on a living organism. Here, a reference electrode and a test electrode provide DC signals indicative of the potential level of the electromagnetic field measured between the reference point and the test point. These signals are provided to an analog-to-digital converter which generates a digital signal as a function thereof, and a processor provides an output signal indicative of a parameter or parameters of the living organism as a function of this digital signal.

Similar biopotential measuring devices are shown by U.S. Pat. Nos. 4,407,300 to Davis, and 4,557,271 and 4,557,273 to Stroller et al. Davis, in particular, discloses the diagnosis of cancer by measuring the electromotive forces generated between two electrodes applied to a subject.

Often, the measurement of biopotentials has been accomplished using an electrode array, with some type of multiplexing system to switch between electrodes in the array. The aforementioned Hirschowitz et al. patent contemplates the use of a plurality of test electrodes, while U.S. Pat. Nos. 4,416,288 to Freeman and 4,486,835 to Bai disclose the use of measuring electrode arrays.

Unfortunately, previous methods for employing biopotentials measured at the surface of a living organism as a diagnostic tool, while basically valid, are predicated upon an overly simplistic hypothesis which does not provide an effective diagnosis for many disease states. Prior methods and devices which implement them operate on the basis that a disease state is indicated by a negative polarity which occurs relative to a reference voltage obtained from another site on the body of a patient, while normal or non-malignant states, in the case of cancer, are indicated by a positive polarity. Based upon this hypothesis, it follows that the detection and diagnosis of disease states can be accomplished by using one measuring electrode situated externally on or near the disease site to provide a measurement of the polarity of the signal received from the site relative to that from the reference site. Where multiple measuring electrodes have been used, their outputs have merely been summed and averaged to obtain one average signal from which a polarity determination is made. This approach can be subject to major deficiencies which lead to diagnostic inaccuracy, particularly where only surface measurements are taken.

First, the polarity of diseased tissue underlying a recording electrode has been found to change over time. This fact results in a potential change which confounds reliable diagnosis when only one external recording electrode is used. Additionally, the polarity of tissue as measured by skin surface recording is dependent not only upon the placement of the recording electrode, but also upon the placement of the reference electrode. Therefore, a measured negative polarity is not necessarily indicative of diseases such as cancer, since polarity at the disease site depends in part on the placement of the reference electrode.

As disease states such as cancer progress, they produce local effects which include changes in vascularization, water content, and cell division rate. These effects alter ionic concentrations which can be measured at the skin surface and within the neoplastic tissues. Other local effects, such as distortions in biologically closed electrical circuits, may occur. A key point to recognize is that these effects do not occur uniformly around the disease site. For example, as a tumor grows and differentiates, it may show wide variations in its vascularity, water content and cell division rate, depending on whether examination occurs at the core of the tumor (which may be necrotic) or at the margins of the tumor (which may contain the most metabolically active cells). The tumor may not respond significantly to growth factors, while the growth factors and the enzymes produced may significantly affect the normal cells surrounding the tumor. Once this fact is recognized, it follows that important electrical indications of disease are going to be seen in the relative voltages recorded from a number of sites at and near a diseased area, and not, as previously assumed, on the direction (positive vs. negative) of polarity.

The accurate measurement of DC biopotentials for sensing or screening for disease, injury or bodily functions is very difficult to accomplish, for the DC potentials to be sensed are of a very low amplitude. Due to factors such as the low DC potentials involved and the innate complexity of biological systems, the collected data signals tend to include a substantial volume of noise which makes accurate analysis difficult. Also, biological systems are notorious for their complexity, nonlinearity and nonpredictability, and wide variations from the norm are not uncommon. For example, DC biopotential signals tend to drift over time, so that if signals are not sensed and analyzed with some rapidity, signal errors due to drift occur.

For the accurate measurement of DC biopotentials for disease diagnosis and screening, electrode and electrode circuit characteristics and electrode placement become important. Factors such as small DC offset potentials in the low millivolt range, which may have little effect on an AC biopotential measurement, such as ECG measurement, can destroy the accuracy of a DC biopotential measurement. For screening applications where many sensing electrodes are used, it is often critical for electrode characteristics to be uniform, for accurate electrode spacing to be maintained and for DC offsets to be substantially eliminated.

Many DC biopotential sensing electrodes are packaged in a pre-gelled state wherein an electrolytic paste or gel is packaged as part of the electrode. The gel may be located in a central gel reservoir consisting of a molded cup, or it may be contained in a dye-cut hole in a foam which encapsulates a gel saturated open cell compressible foam column. In most instances, the pre-gelled electrodes are sold ready for use with an electrically conductive material such as metal or a metal chloride in contact with the electrolyte gel.

A pre-gelled electrode system is generally not a battery by itself, but forms a part of a battery-system consisting of two or more electrodes placed on the body. In such a system, a complex battery is formed consisting of many interactive components including the electrode material (frequently silver/silver chloride), the electrode gel, internal body chemistry and external skin conditions, skin preparation, temperature, air condition and chemistry, etc. Obviously, some of these factors are not subject to control, but in order to get the best data possible, especially in instances where DC biopotentials are of interest, artifacts, such as DC offsets, should be reduced to the lowest level. Most pre-gelled electrodes when introduced in the battery system outlined above contribute some unwanted DC voltage (polarization effect) to biopotential measurements. It is important to lower the possibility of such DC artifacts occurring to a degree sufficient to preclude them from having a substantial adverse effect on biopotential measurements.

The design and performance characteristics for an effective DC biopotential electrode are different from those of electrodes designed for measuring alternating current (AC) signals such as those used with electrocardiology (ECG) and electroencephalography (EEG). For example, U.S. national standards for single use ECG electrodes allow the DC offset of an electrode pair (i.e., the spurious DC current generated by electrochemical interactions between electrode components) to be as high as 100 millivolts (ANSI/AAMI standard). Since effective use of DC signals for cancer diagnosis requires discrimination at the one millivolt level, standards for ECG electrodes are grossly excessive. ECG electrodes are intended for AC measurements which are not significantly affected by DC offset voltages in the electrode to the degree that DC biopotential measurements are adversely affected by such offset voltages. The traditional view taken in the manufacture of ECG pregelled electrodes is that to reduce DC offset, one must sacrifice AC impedance, and since a low AC impedance is most important in an ECG pregelled electrode, the DC offset voltage is tolerated. However, for highly accurate DC biopotential measurements, both the DC offset potential and the AC impedance for the electrode must be low.

When DC biopotential measurements are taken from the skin of a subject with conventional ECG electrodes, sweat gland activity creates noise which tends to mask the sensed DC signal, and the provision of an electrode structure to minimize this noise is essential.

If a pre-gelled electrode array is to be used effectively for disease detection, such as breast cancer screening, the array will require a relatively large number of spaced electrodes to cover substantially the entire surface of the breast. Not only must each of these electrodes be free from error causing offset potentials before use, but the electrodes must maintain contact with the curved surface of the breast without movement during the screening procedure and must maintain a predetermined array formation with specified electrode spacing. Consistent location and orientation of the electrical channels connected to the respective electrodes must also be maintained to prevent incorrect connection to the electrodes and to maintain positive contact between the electrodes and the electrical channel leads therefor.

In the past, these objectives have not been met with an apparatus which could be rapidly applied and worn comfortably by a patient, and which also produces reliable DC measurements.

The key to effective measurement and analysis of direct current skin potentials is absolute maintenance of signal integrity from the skin surface to the signal processing components of the measuring unit. This is especially critical due to the inherent low amplitude of biologic DC potentials. At any point in the electronic path from the skin sensing electrode to the measuring unit, potential exists for noise to intrude upon signal, thereby degrading diagnostically useful information.

DISCLOSURE OF THE INVENTION

It is a primary object of the present invention to provide a novel and improved biopotential sensing electrode having a low DC offset and a low AC impedance.

Another object of the present invention is to provide a novel and improved gel or cream for use as an electroconductive medium in a DC biopotential sensing electrode which transmits ions from the skin of a subject to an electrode sensing element wherein the gel or cream includes a chloride ion content which is within the range of chloride ion that is in isotonic or hypertonic fluids.

A further object of the present invention is to provide a novel and improved DC biopotential sensing electrode having dual conductive paths through the electrical conductive elements of the electrode.

Yet another object of the present invention is to provide a novel and improved gel or cream for a pre-gelled DC biopotential electrode having a high chloride ion content. The electrode structure is formed to be resistant to corrosion caused by ions in the gel or cream.

BEST MODE FOR CARRYING OUT THE INVENTION

Figure 1:
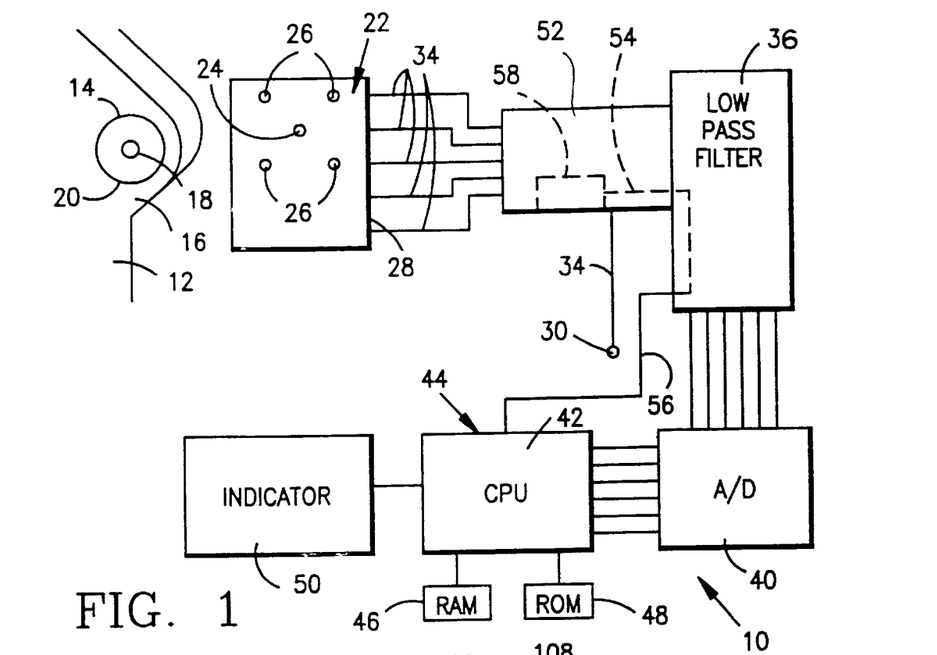
FIG. 1 is a block diagram of the apparatus for disease, injury and bodily condition screening or sensing with the DC biopotential sensing electrode assembly of the present invention.

FIG. 1 discloses a basic block diagram of the measuring apparatus 10 for performing an analysis for indicating the presence, absence or state of a condition at a test site on a human or animal subject. For purposes of illustration, the apparatus 10 will be described in connection with methods involving the screening or sensing of breast cancer. However, it should be recognized that the apparatus can be similarly employed for providing an indication of disease, injury or other body condition of a living human or animal.

In FIG. 1, a human subject 12 may have a cancerous lesion 14 on one breast 16. This cancerous lesion has a core 18 and an outer zone 20 surrounding the core where various differing local effects, such as changes in vascularization, water content and cell division rate occur. Assuming first, for purposes of discussion, that the location of the lesion 14 is now known, and the device 10 is to be used to screen the breast 16 to determine whether or not a disease condition exists, skin surface potentials will be measured in an area of the breast, including the zone 20 using an electrode array 22. In FIG. 1, the electrode array includes a central electrode 24 surrounded by four peripheral electrodes 26, all of which are skin surface electrodes. However, this invention contemplates the use of a variety of different electrode arrays depending upon the intended application for which the device 10 is used. For example, in the diagnosis of clinically symptomatic breast or skin lesions, the electrode array should cover various areas of the lesion as well as relatively normal tissue near the lesion site. For breast cancer screening (where patients are asymptomatic), the array should give maximum coverage of the entire breast surface. The aim in both of these areas is to measure the gradient of electrical activity which occurs as a function of the underlying biological activity of the organ system. The number of electrodes used in the measurement will also be a function of specific application, and breast cancer screening may require the use of as few as twelve or as many as sixty or more electrodes for each breast, while in screening for prostate cancer, as few as two measurement electrodes might be used.

The core electrode 24 and the peripheral electrodes 26 are mounted upon a flexible backing sheet 28 which permits the electrodes to be positioned against the curved surface of the breast 16 while still maintaining the position of the electrodes in predetermined pattern. However, other electrode arrays may be employed wherein each individual electrode can be individually positioned, and the relative position between electrodes can be altered. The electrode array 22 is used in conjunction with one or more reference skin surface electrodes 30, and all of these electrodes are of a type used for detecting the potential level of the DC electromagnetic field present in a living organism.

The device 10 is shown as a multi-channel device having electrode leads 34 extending separately from the central electrode 24, the peripheral electrodes 26, and the reference electrode 30 to a low pass filter amplifier 36. This filter amplifier operates to remove some undesirable high frequency AC components which appear on the slowly varying DC voltage signal outputs provided by each of the electrodes as a result of the electromagnetic field measurement.

The output from the filter amplifier 36 is provided to an analog-to-digital converter 40 which converts each analog signal received thereby to a digital signal to be provided to the input of a central processing unit (CPU) 42. Of course, for some applications, the central processing unit may respond directly to analog input signals or to digital or other coded signals produced directly by the electrode array 22, and in such cases, the analog to digital converter 40 and possibly even the filter 36 would be eliminated and the output from the electrode array would input directly to the CPU. The central processing unit is a component of a central control unit indicated generally at 44 which includes RAM and ROM memories 46 and 48. Digital input data from the analog-to-digital converter 40 is stored in memory and is processed by the CPU 42 in accordance with a stored program to perform various pattern recognition methods to be described. The digital signals may be subjected to digital filtering by the CPU before processing. The information derived by the CPU as a result of this processing is then fed to a suitable indicator device 50 which may constitute a printer, a CRT display device, a storage tape or disc, or a combination of such conventional indicators.

It is important that no biopotential measurements be taken using the device 10 if an array containing electrodes designed for sensing DC biopotentials is not connected to provide the electrode array 22 and the reference electrode 30. One structure for accomplishing this incorporates the leads 34 into a cable 52 which is used to removably connect the electrode array 22 and the reference electrode 30 to the low pass filter amplifier 36. This cable can be a multichannel cable or a single channel cable, depending upon whether or not electrode multiplexing is employed. A conventional connector, not shown, is provided to connect one end of the cable to the low pass filter 36, or with a single channel filter, the connector may be plugged to a sequencing switch. Each cable lead 34 is connected to the output terminal for one of the electrodes in the electrode array 22.

When the cable 52 is connected to the low pass filter amplifier 36, a separate connection is made between a conductor 54 within the cable and a conductor 56 leading directly to the CPU 42. The conductor 54 leads to an address identification chip 58 of known type which responds to an address interrogation signal provided over the conductor 54 to the address chip. The proper address interrogation signal is stored in the memory for the central control unit 44 and is sent over the conductor 56 by the CPU 42 when the apparatus 10 is initially activated. If this interrogation signal corresponds to a signal to which the address chip 58 responds, then a response from the address chip is passed by the conductors 54 and 56 back to the CPU 42 and the CPU initiates a measurement operation in response to a control program stored in the memory for the central control unit. Alternatively, if the wrong address chip, no address chip or no electrode array connection is present, no response is received from the address interrogation signal and the CPU 42 does not proceed with the stored control program.

In addition to the address chip 58, the central control unit 44 can be made responsive to other parameters in the electrode array 22 during an initial test period to assure that an acceptable electrode array is in place before a measurement program is begun. As has been previously indicated, the presence of an offset potential in the electrode array is detrimental to the accuracy of DC biopotential measurements, and the magnitude of this offset potential can be measured during the test period of the apparatus 10. If the measured offset potential is less than a predetermined level, then the CPU may continue with a measurement operation in response to the stored control program, but if the offset potential exceeds the predetermined level, the measurement operation is not initiated by the CPU.

The electrodes which are used as the electrodes 24, 26 and 30 should be manufactured to specific electrical tolerances if they are to be effectively used to provide accurate DC biopotential measurements. The electrical characteristics of each electrode are determined by elements of construction such as electrode size, the type of gel or cream used, and the types of metals and other materials used in constructing the electrode. These electrical characteristics may be measured in the same manner as the offset potential, and the measurement operation can be cancelled by the CPU if the proper electrode characteristics are not present.

It is important to recognize that the CPU 42 can be programmed to run identification tests on a variety of electrode combinations, since diverse DC biopotential measurement applications require the use of different numbers of electrodes. Thus, the electrical characteristics of as few as two electrodes, a reference and a measurement electrode, plus a plurality of acceptable electrode array combinations would be stored in the memory of the control unit 44. It is also possible to provide each individual electrode with an address identification chip 58 having a lead or terminal 56 which could plug into a test block connected to the CPU. This would permit each individual electrode to be used during a measurement operation to be identified by the CPU 42 during an initialization operation.

Although the unit 58 has been identified as an address identification chip, this unit constitutes any structure which responds to an interrogation signal in a definable manner. For example, the unit 58 could be formed by a particular material having a specific response characteristic to an interrogation signal, and this material could actually be one which is used in the construction of the individual electrodes.

The operation of the apparatus 10 will be clearly understood from a brief consideration of the broad method steps of the invention which the device is intended to perform. The electrode array 22 is positioned with electrodes 24 and 26 located over various diverse areas of a test site, and the reference electrode 30 is then brought into contact with the skin of the subject in spaced relationship to the electrode arrays. This reference electrode might, for example, be brought into contact with a hand of the subject. The electromagnetic field between the reference electrode and each of the electrodes 24 and 26 is measured, converted to a digital signal and stored for processing by the control unit 44. The program control for the central processor unit 42 causes a plurality of these measurements to be taken over a period of time, and the measurements on all channels are taken repetitively during a predetermined measurement time or test period. Sequential measurements between the reference electrode and one of the electrodes in the array 22 are taken until each channel is sampled, and then the sequential measurement is repeated throughout the duration of the predetermined test period. In prior art units, a plurality of measurements have been taken over a period of time and often from a plurality of electrodes, but then these plural measurements are merely averaged to provide a single average output indication. In accordance with the method of the present invention, the measurement indications on each individual channel are not averaged with those from other channels, but are instead kept separate and averaged by channel within the CPU 42 at the end of the test period. For the duration of a single test period, for example, for the five measurement channels shown, the CPU will obtain five average signals indicative of the average electromagnetic field for the test period between the reference electrode 30 and each of the electrodes 24 and 26 in the electrode array 22. Of course, more reference electrodes can be used, although only one reference electrode has been shown for purposes of illustration.

Having once obtained an average signal level indication for each channel, the results of the measurements taken at multiple sites are analyzed in terms of a mathematical analysis to determine the relationships between the average signal values obtained. It has been found that the result of such an analysis is that a subset of relationships can be obtained which are indicative of the presence of more serious disease, injury or other condition, while a different subset might be obtained which will be indicative of the absence of such conditions.

One important relationship to be obtained is designated the maximum voltage differential (MVD), which is defined as the minimum average voltage value obtained during the test period subtracted from the maximum average voltage value obtained for the same period where two or more electrodes are recording DC potentials from a test site relative to the same reference. Thus, for each predetermined test period, the lowest average voltage level indication obtained on any of the channels is subtracted from the highest average voltage level indication obtained on any of the channels to obtain an MVD voltage level. If this MVD voltage level is above a desired level <x, then a disease condition, such as a malignancy, injury or other condition could be indicated. Similarly, if the average taken over the measurement period from one channel is an abnormally low value <y, the presence of this abnormally low individual electrode reading (IER) could be indicative of a disease condition, injury or other condition. These primary indicators may be further analyzed to reduce the number of false positive diagnosis which may be falsely identified on the basis of high MVD or low IER readings.

Figure 2:
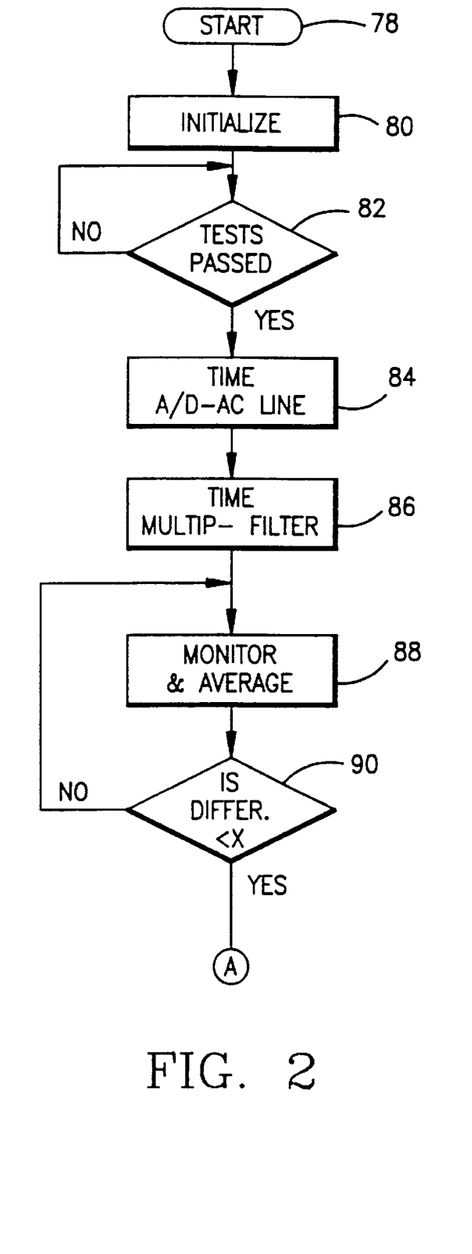
FIG. 2 is a flow diagram illustrating the operation of the apparatus of FIG. 1.
Figure 3:
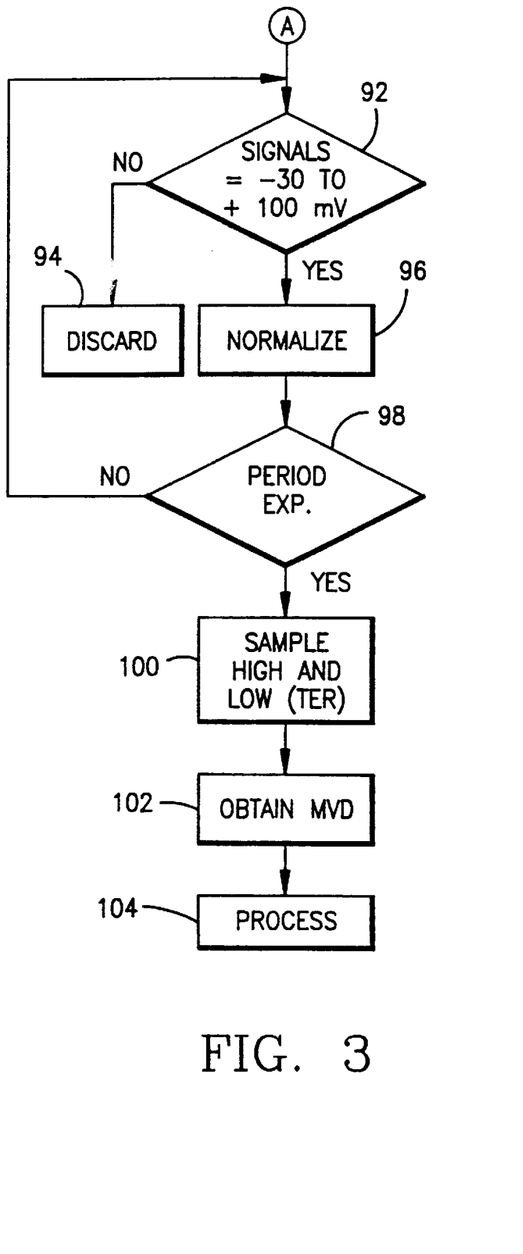
FIG. 3 is a flow diagram illustrating the operation of the apparatus of FIG. 1.

The general overall operation of the central processing unit 42 will best be understood with reference to the flow diagrams of FIGS. 2 and 3. The operation of the unit 10 is started by a suitable start switch as indicated at 78 to energize the central processing unit 42, and this triggers an initiate state 80. In the initiate state, the various components of the device 10 are automatically brought to an operating mode, with for example, the indicator 50 being activated while various control registers for the central processing unit are reset to a desired state.

Subsequently, a test period is initiated at 82 wherein the various components of the system are tested for proper operability. During this test period, the electrode array 22 may also be tested to make certain that electrodes are being used which accurately measure DC biopotentials. This would involve interrogation of the address chip 58 and possibly the testing for other electrode characteristics. The address chip may be included in a disposable cable connector to be subsequently described, and it can be important that this cable connector be adapted for only one use. Therefore, the central processing unit may have the ability to disable the address chip once a proper address is received so that the cable connector cannot be reused with improper electrodes to provide a new address signal. This can be accomplished in a number of ways. For example, the address chip 58 may be an EE PROM containing the address combined with a signal activated erase circuit for the EE PROM. Once the central processor receives the proper address, it would send a command signal to the erase circuit to erase the EE PROM.

Another simple deactivation circuit would include a small fuse unit in the line 54 portion of a cable connector. Once the central processor receives the proper address, it would send a command signal over the line 56 to burn out or blow the fuse circuit and disconnect the address chip 58.

If all system components test out properly during the system test period, then timing of the analog to digital converter in accordance with the AC line frequency begins at 84 and the timing of any switching systems or multiplexors begins at 86. It is now possible to monitor the biopotential signals from a test area during a monitoring period begun at 88. During this monitoring period, conditions in the test area contacted by the electrode array 22 are stabilized so that subsequent reliable measurements of DC biopotentials can be obtained. Since the stabilization period for different subjects varies, some unknown time period must lapse before reliable measurements of DC biopotentials are obtained. Thus, at 88, a predetermined monitoring period is initiated, and the signals on all channels are monitored and averaged. Then, at the end of the initial monitoring period, the individual sample voltages are compared to the average of all voltages sampled during the measurement period to obtain a differential, and if the differential is greater than a predetermined value x, then sufficient signal stabilization has not occurred during the monitoring period and a new monitoring period is initiated. Conversely, if the differential signals are less than the predetermined value x, then the monitoring period is terminated and a test period is initiated.

With reference to FIG. 3, during the test period the digitized signals received from the various sequenced channels are monitored at 92 to determine whether or not each biopotential represented by the signals is within the range of from −30 to +100 millivolts. Digitized signals indicative of DC signals outside this range are discarded at 94 and the remaining signals are used to provide an average or normalized value for each channel at 96. The averaged value for each channel is obtained by summing the values obtained for that channel during the test period and dividing the sum by the number of measurements taken. Then, at 98, the central processor unit determines whether the test period has expired and the desired number of measurements have been taken, and if not, the collection of measurement samples or values continues.

Once the measurement or test period has expired, a final average value for each channel derived from the measurements taken during the span of the test period is available, and from these average values, the highest and lowest average value obtain during the test period is sampled at 100. The lowest average channel value is subtracted from the highest average channel value at 102 to obtain a maximum voltage differential value. This maximum voltage differential value is then processed at 104 to indicate the presence or absence of a disease, injury, or other bodily condition, and during processing, can be compared with previously obtained differential values to determine the efficacy of treatment or the progress of a disease, injury or other bodily condition. The differential value may also be used to indicate the occurrence of a number of normal bodily functions such as ovulation, and normal or abnormal labor conditions. In addition, for pattern recognition purposes, the digital signals stored by the central control unit and the average signals for each channel can be processed at 104 in a manner to be described.

A major design consideration for an effective DC biopotential measurement device 10 is to make the input impedance many times higher than that produced by the skin and sensor interfaces. Failure to do so results in decreased signal amplitude and, most important, loss of low frequency (e.g., DC) information. Sampling of DC potentials (e.g., number of samples and over what time period) ideally should be under computer control and it is here that microprocessor technology is utilized to its fullest. In digital systems, selection of the optimal sampling regimen is a balance between two factors:

1) acquiring enough samples per unit time to be representative of depolarization due to increased proliferation and 2) avoidance of taking samples over an extended time frame which might reflect DC drift. In other words, measuring the precise time slice of DC activity representative of cell proliferation is an important design consideration. It can be shown that reducing the number of DC samples per unit time can lead to irreproducible DC measurements.

Computer control of signal acquisition allows each electrode to be sampled via a multiplexed system. In a multiplexed system, each electrode output voltage is sampled multiple times in precise sequence, using a single amplifier or filter amplifier. Because only one amplifier (rather than multiple) amplifiers is used, this system ensures that individual channels are calibrated to each other. The resultant individual voltages are then averaged to provide a composite voltage for each electrode site. Since all individual samples can be stored and processed digitally, averaged voltages and variability in voltages over time can be analyzed for signal integrity. Comparisons of the averaged voltages are then used to identify areas of relative depolarization on the breast surfaces.

The fastest multiplexed DC measurement system currently available for breast electropotential evaluation can scan up to 96 electrodes 150 times over a 1.5 minute period. The array of sensors used in previous diagnostic studies consists of 16 measuring electrodes, which can be scanned 150 times each in about 18 seconds.

Pattern recognition of DC potentials is enhanced by effective filtering of the periodic electrical signals produced by cardiac and neural activity. These periodic signals typically range from about 1 Hz for cardiac signals to as much as 10 kHz for some neural signals. State-of-the-art digital filters are effective in keeping bandpass below 1 Hz. After filtering and averaging, DC voltages can be stored on tape or disk, displayed on a CRT, or printed. Typically, averaged voltages corresponding to each electrode are displayed, along with two measures of variability. These two measures are the Modified Range (MRNG) and test Reliability (REL). These measures can provide important information regarding signal voltage samples. It is a modified range because CPU programming sets a limit of 20 mV (i.e., +/−10 mV from the averaged voltage). If MRNG exceeds 20 mV, the individual voltages which exceed this value are filtered out and MRNG is recalculated. REL is expressed as a percentage of the 150 individual voltages and indicates how many individual voltages required filtering. High MRNG and low REL values may indicate that signal integrity has been compromised, perhaps by an electrode which has become disconnected from the patient.

One additional advantage of multiple electrode arrays is the richness of the data base which results from each patient test. As opposed to many other quantitative diagnostic and screening tests, such as serum assays, surface potential arrays provide multidimensional data. The key to effective diagnosis then becomes pattern recognition, which has become a science unto itself with the advent of sophisticated pattern recognition computer programs. Because concurrent measurements are made from a multiplicity of sites, surface potential analysis provides information across several dimensions. Differentials can be calculated from the entire breast or specific regions within the breast. Potential differences also can be compared between the two breasts (the between breast differential), or between corresponding pairs of sensors (mirror site differential). This wealth of quantitative information presents both an opportunity and a challenge to the goal of extracting signal patterns from an inherently noisy biological environment.

One approach to this kind of pattern recognition problem is to employ linear discriminant analysis. This can be effective in establishing a set of parameters which predict a given state, such as malignant vs benign disease. Its predictive value decreases if there are thresholds in the data. If thresholds in the data do exist, then nonlinear discriminant methods are called for. One recently developed approach is tree analysis, such as CART (Breiman et al. 1984), PIMPLE (Breiman, 1991), MARS, (Friedman, 1991), and SUPPORT (Chaudhuri, 1994). Decision trees, such as those produced by CART (Classification and Regression Trees) lead to a binary outcome (e.g., cancer vs benign states). Each decision point in the tree is referred to as a node in which optimal cut-off values are established based on variables considered for the study. CART arrives at the best decision tree for a data set first by constructing a very large tree using certain optimal criteria, and then pruning back the branches to reveal the key predictive variables. CART trees can be constructed with two parameters which can be controlled by the user. One parameter is tree complexity, which is used to penalize a non-significant large tree, which may not be predictive of future data sets. The other parameter is the cost ratio between false negative and false positive results, which in essence allows the user to determine the trade-off between test sensitivity and specificity.

The ability to trade sensitivity against specificity is a powerful advantage of electropotential analysis. In certain situations, such as disease screening, a high sensitivity is desired and reduced specificity can be tolerated. In diagnostic situations, it may be desirable for the test characteristic to feature high specificity. The use of CART allows objective control over these parameters.

Another nonlinear method which has gained popularity recently is the use of neural networks. As opposed to decision trees, which function as a process flow from node to node, neural network nodes (referred to as neurons) are arranged in two or three parallel levels. Information from one level can feed back to influence decision points at other levels in the network until a complex path of decision is made which can discriminate between disease states.

Regardless of which pattern recognition strategy is adopted, assessing the predictiveness of the decision matrix for new populations is essential. The traditional approach has been to collect data for a subgroup of patients, develop the decision matrix, and then validate the matrix on a new group of patients. The former group is referred to as the training data set and the latter group is referred to as the test data set. The decision matrix developed for the training data set is cross-validated for the test data set. In this way cross validation provides an index of how well the test sample will predict for the population for which the test method was developed for. Unfortunately, this strategy wastes resources by requiring the study to be run twice. In most studies data is a precious resource, and it is advantageous to use the largest possible population for development of the decision matrix. Therefore, statisticians have developed many data resampling methods which utilize the same sample for decision matrix formation and validation. The first resampling techniques, referred to as the jackknife and resampling cross validation, have been studied for several years. A newer resampling method, called the bootstrap (Efron, 1979) has been one of the most intensively researched methods in statistics during the past 15 years. The method consists of treating the existing sample as the population. One uses a computer to draw many samples from the test population in order to measure the bias between the sample and the population. Resampling cross validation calls for reiteratively sampling random segments of the data to be used for decision matrix formation, with residual segments being used for validation. For example, a decision matrix is constructed on a 90% sample of the population and then validated on the remaining 10%. Next, a different 90% sample is chosen at random and validated on the remaining 10%. The process is done recursively for numerous 90/10 splits of the data set. The total error generated by all the recursive samplings of the data base can be used as a surrogate for traditional validation techniques.

Once a decision matrix for disease diagnosis has been validated, it is programmed into the software for the CPU 42. This allows the test result to occur in real time. For each patient test, output from the device is anticipated to include averaged potentials from each electrode (along with MRNG and REL data), as well as a probability estimate as to whether the breast electropotential readings indicate the existence of malignancy. The physician would then use this information within the context the patient's total medical profile, which includes results from other tests and medical history to determine case management.

The DC biopotential sensing electrodes 24, 26 and 30 are responsible for transmitting ionic current from the skin of a subject through an electroconductive medium contained in the electrode, such as a cream or gel, which forms a conductive bridge between the skin surface and an electrode sensor element. The sensor element transduces ionic conduction to metallic conduction, and the resultant signal is then relayed by a cable system from the output of the sensing electrode.

Ions from the skin surface are driven into the electroconductive medium by electromotive force, or the physical propensity of ionic concentrations to equilibrate. At the gel or cream and sensor interface, a charge gradient between ions in the gel or cream and the discharge of ions from the sensor is formed. This has been referred to as the electrical double layer and can be visualized as two parallel sheets of charge with opposite sign. Maintenance of a stable double layer is an integral part of keeping noise to a minimum in DC measurement systems.

Another source of potential noise is resistance in a circuit, often referred to as Johnson noise, named after its discoverer. Resistance in any circuit creates spurious wide band voltages which result from the random motion of charge carriers in the conductor. Johnson noise can be ameliorated by using low resistance sensing electrodes and limiting the bandwidth of the measuring apparatus. Failure to control Johnson noise limits the level of minimum signal which is detectable.

The optimal single-use sensing electrode for biologic DC measurement requires both low DC offset and low resistance. This has been accomplished in accordance with the present invention by designing a sensing electrode which utilizes the excellent conductive properties of a novel low viscosity, high electrolyte content gel or cream, along with only one metallic component, such as silver. Such a design circumvents the problem of a dissimilar metals reaction which can be exacerbated by use of low viscosity, high electrolyte content gels and creams. Under strict manufacturing controls, sensors of this type can be made with DC offsets less than 0.5 mV and with very low impedance characteristics.

To compensate for sodium chloride present on the skin of a patient, which tends to mask sensed DC biopotential signals, a DC biopotential sensing electrode has been designed which incorporates an electroconductive medium in the form of a gel or cream which has a chloride ion content within or higher than the range of chloride ion present in isotonic or hypertonic fluids. This chloride ion content includes a substantial amount of chloride ions derived from sodium chloride as well as an equal or greater amount of chloride ion derived from other ionic chloride salts, such as potassium chloride as well as calcium chloride, and this total chloride ion content is combined in a cream or gel formed from 8% to 35% solids mixed with water. The water must be free of impurities, such as heavy metals, which interfere with the DC biopotential signal sensed by the sensing electrode, and preferably pharmaceutical grade water is used in the formation of the gel or cream. The gel or cream is formed to have a pH within a range of 4 to 6.5, and a total chloride ion content within a range of 6–15 grams chloride ion per hundred grams of electroconductive medium. The total chloride ion content is preferably no more than 12 g chloride ion per 100 g of electroconductive medium; the minimum amount is preferably 7 or 8 g chloride ion per 100 g of electroconductive medium, depending on the physical form of the medium. The preferred lower limit is 7 g chloride ion per 100 g of cream and 8 g chloride ion per 100 g of gel. The conductivity of the gel or cream is within a range of from 22,000 to 120,000 micromhos; the micromho being the inverse of impedance indicated by the ohm. Preferably, the conductivity of electroconductive cream is within a range of from 22,000 to 50,000 micromhos and the conductivity of electroconductive gel is within a range of from 100,000 to 120,000 micromhos.

The following examples are illustrative of the invention. Numerous other formulations that fall within the ranges of components taught by the specification of the patent will be readily apparent to those skilled in the art.

EXAMPLE 1

Formulation and Manufacture of Electroconductive Medium in Cream Form

The following materials are weighed out and charged into individual, cleaned, heat resistant containers of suitable size.

| COMPONENT | QUANTITY (g/100 g cream) |
|---|---|
| Water: USP purified | 63.4 g |
| Sodium Chloride (ACS) | 6.7–8.1 g |
| Potassium Chloride (ACS) | 2.9–3.5 g |
| Calcium Chloride Dihydrate (ACS) | 3.0–3.6 g |
| Propylene Glycol | 7.9–9.7 g |
| Propylene Glycol Stearate, tech. grade | 2.8–3.4 g |
| Glycerol Monostearate, tech. grade | 2.6–3.2 g |
| Stearyl/Cetyl Alcohol blend | 0.9–1.1 g |
| Minerai Oil | 6.3–7.7 g |
| Methylparaben | q.s. to pass USP/APET |
| Propylparaben | q.s. to pass USP/APET |
| Butylparaben | q.s. to pass USP/APET |

A stainless steel kettle, such as Groen model No. KRE/1-40 with heating capability and appropriate capacity and rating is selected. The kettle must be equipped with a built-in agitator or be capable of having an add-on agitator system added to it. A typical synthesis of a ≈100 kg batch of electroconductive cream is detailed below with the reagents listed above scaled accordingly.

The weighed USP purified water is added to the tank mixer and stirred. The kettle is heated until a temperature of 60°+/−2° C. is achieved. Sodium chloride is then slowly added over a 5 minute period to the kettle and the contents of the kettle are mixed thoroughly for 15 minutes after the addition is completed or until the sodium chloride is completely dissolved. Heating of the kettle is continued with the temperature maintained at 60°+/−2° C. Potassium chloride is slowly added next over a 5 minute period and mixed thoroughly for 15 minutes after addition is completed or until the potassium chloride is completely dissolved. Heating is maintained at 60°+/−2° C. Calcium chloride dihydrate is then slowly added over a 5 minute period and the contents of the kettle mixed thoroughly for 15 minutes after the addition is completed or until the calcium chloride dihydrate is completely dissolved. Care is again taken to maintain the temperature of the mixture at 60°+/−2° C.

The parabens (methylparabens, propylparabens and butylparabens) are then slowly added to the kettle over a 5 minute period and mixed thoroughly with the contents of the kettle for 5 minutes. The temperature of the mixture is maintained at 60°+/−2° C. Propylene glycol is then next slowly added over a 5 minute period and the contents of the kettle are mixed thoroughly for 5 minutes maintaining a temperature of 60°+/−2° C. Glycerol monostearate is slowly added over a 5 minute period and mixed thoroughly with the contents of the kettle for 5 minutes with the temperature maintained at 60°+/−2° C. Polyethylene glycerol stearate is melted and slowly added to the contents of the kettle and the contents mixed thoroughly for 5 minutes or until all of the stearate has dispersed. The temperature is held at 60°+/−2° C. Stearyl/cetyl alcohol blend is then melted and added in a thin stream to the contents of the kettle over a 5 minute period and mixed thoroughly for 5 minutes until all of the alcohol blend has melted and dispersed. The temperature is held at 60°+/−2° C. Finally, the mineral oil is added in a thin stream over a 5 minute period and mixed thoroughly with the contents of the kettle with the temperature held at 60°+/−2° C.

After all of the ingredients of the cream formulation have been added as specified above, the contents of the kettle are stirred thoroughly and slowly allowed to cool to 48°+/−2° C. Stirring is continued and the contents of the kettle cooled to 25°+/−5° C. The complete cream is then removed from the kettle and packaged in tightly sealed containers.

For the key component concentrations, the following tabulated nominal molarities and weights of component (in g/100 g) are preferred. The components may range from 2.33–2.92 g $Na^+$, 0.81–0.93 g $Ca^{+2}$, 1.58–1.80 g $K^+$ and 7.6–9.06 g Cl per 100 g of cream and still yield clinically acceptable results for this particular formulation. The final cream exhibits a conductivity of 24,800–39,400 micromhos and a viscosity at 25° C. of 14,000–16,000 cps.

| COMPONENT | NOMINAL MOLARITY | g/100 g |
|---|---|---|
| $Na^+$ | 1.26 M | 2.9 |
| $Ca^{+2}$ | 0.23 M | 0.9 |
| $K^+$ | 0.43 M | 1.7 |
| Cl | 2.2 M | 7.6 |
| Propylene Glycol | 1.15 M | 8.8 |
| Preservative Effectiveness Test | USP XXIII | Pass |

EXAMPLE 2

Formulation and Manufacutre of Electroconductive Medium in Gel Form

The following materials are weighed out and charged into individual, cleaned, heat resistant containers of suitable size.

| COMPONENT | QUANTITY (g/L) | QUANTITY (g/100 g gel) |
|---|---|---|
| Water: USP purified | 1 L | 75.8 g |
| Sodium Chloride (ACS) | 45.0–54.3 g | 3.38–4.12 g |
| Potassium Chloride (ACS) | 134.1–162.5 g | 10.14–12.38 g |
| Calcium Chloride Dihydrate (ACS) | 88.2–108.8 g | 6.76–8.26 g |
| Hydroxyethyl Cellulose, NF | 22.0 g | 1.51–1.83 g |

15

-continued

| COMPONENT | QUANTITY (g/L) | QUANTITY (g/100 g gel) |
|---|---|---|
| [Natrosol 250 HHR] Preservative System | Appropriate System To Pass USP [APET] | Appropriate System To Pass USP [APET] |

A stainless steel kettle with heating capability and appropriate capacity and rating is selected. The kettle must be equipped with a built-in agitator or be capable of having an add-on agitator system added to it. A typical synthesis of a≈100 kg batch of electroconductive gel is detailed below with the reagents listed above scaled accordingly using either a g/L or g/100 g formulation.

The weighed USP purified water is added to the tank mixer and stirred. The kettle is heated until a temperature of 34°+/−8° C. is achieved. Potassium chloride is then slowly added over a 5 minute period to the kettle and the contents of the kettle are mixed thoroughly for 15 minutes after the addition is completed. Heating of the kettle is continued with the temperature maintained at 38°+/−4° C. Sodium chloride is slowly added next over a 5 minute period and mixed thoroughly for 15 minutes after addition is completed. Calcium chloride dihydrate is then slowly added over a 5 minute period and the contents of the kettle mixed thoroughly for 30 minutes after the addition is completed. The temperature is then checked and maintained at 38°+/−4° C.

The pH of the contents of the kettle are then adjusted to pH=8 using 5 mL aliquots of 1% NaOH base solution. The kettle is then uncovered and Natrosol is slowly added over a 10 minute period using a fine-mesh stainless steel sifter in constant motion so as to not cause clumping of the thickener. The pH of the mixture is then adjusted to pH=7 using 100 ml aliquots of 1% NaOH buffer. The mixture is then stirred for 30 minutes. The temperature of the kettle is raised to 54°+/−5° C. and then heating is stopped. The kettle is then covered and the contents mixed thoroughly for 3 hours. The gel is allowed to cool. After 24 hours, the pH of the mixture is checked while stirring and is adjusted to a target pH of 6.5 using 1% NaOH, if necessary. The completed gel is then removed from the kettle and packaged in tightly sealed containers.

For the key component concentrations, the following tabulated nominal molarities and weights of component (in g/100 g) are preferred. The components may range from 1.44–1.69 g $Na^+$, 2.10–2.30 g $Ca^{+2}$, 5.9–6.53 g $K^+$ and 10.70–11.36 g Cl per 100 g of gel and still yield clinically acceptable results for this particular formulation. The final gel exhibits a conductivity of 108,800–119,800 micromhos and a viscosity at 25° C. of 51,200–58,400 cps.

| CATION | NOMINAL MOLARITY | g/100 g |
|---|---|---|
| $Na^+$ | 0.85 M | 1.47 |
| $Ca^{+2}$ | 0.67 M | 2.05 |
| $K^+$ | 1.99 M | 5.90 |
| Cl | 3.20 M | 11.25 |
| Preservative Effectiveness Test | USP XXIII | Pass |

The chloride ion content in the electroconductive medium of the present invention is much higher than that in conventional pregelled AC biopotential sensing electrodes, and this high chloride ion content will rapidly cause corrosion to occur in a conventional electrode rendering the electrode useless after a minimal shelf life period. The novel DC biopotential sensing electrode of the present invention indicated generally at 106 in FIGS. 4 and 5, has been uniquely designed to have a long shelf life in spite of the high chloride ion content of the electroconductive medium used in the electrode and to exhibit both a low DC offset and a low AC impedance.

With reference to FIGS. 4–7, the DC biopotential sensing electrode 106 of the present invention includes a sensor element 108 having a sensor body 110. The sensor body is formed from a round sensor disc 112 and a mounting pin 114 which projects outwardly from the sensor disc. A first, lower surface 116 of the sensor disc provides an interface surface for contact with the electroconductive medium contained in the electrode, while a second opposed surface 118 from which the mounting pin projects provides a sealing surface for sealing the electroconductive medium within the electrode. The diameter of the sensor disc can affect the DC biopotentials sensed, and preferably the diameter is within a range of 0.39–0.43 inches.

The biopotential sensing electrode 106 includes only a single metal component which is highly resistant to corrosion when subjected to the high chloride ion content of the electroconductive medium for the electrode, for the inclusion of more than one metal would result in a bimetallic action that would enhance corrosion caused by chloride ion. Consequently, the body 110 of the sensor element 108 is formed of a nonmetallic material 120, such as plastic, glass, or a combination of both, and is then coated uniformly with a very thin coating 122 of an electrically conductive metal. The metal coating 122 is preferably only 1 mil. in thickness and should have a thickness within a range of 0.5 to 1.5 mil. If the coating is thinner, it becomes too thin to provide an even coating and to achieve equilibrium with the electroconductive medium, and if the coating is thicker, electrical resistance is increased to an undesirable level.

Figures 4, 5:
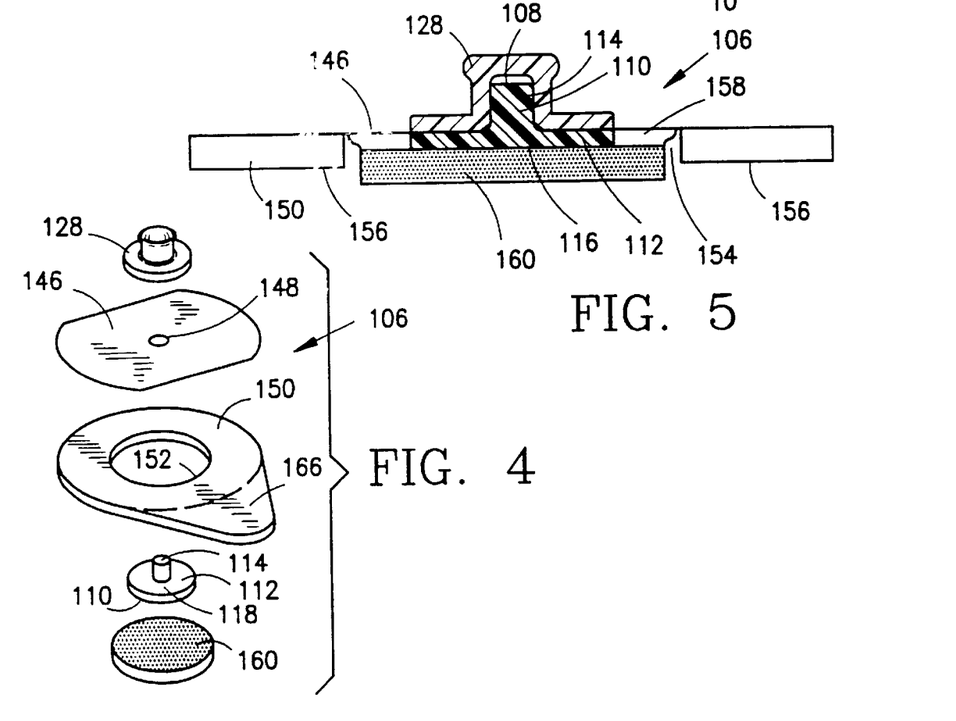
FIG. 4 is an exploded view of a DC biopotential sensing electrode for use with the apparatus of FIG. 1.
FIG. 5 is a cross sectional view of the electrode of FIG. 4.

The metal coating 122 must evenly coat all surfaces of the nonmetallic material 120 and provide an unbroken layer of substantially uniform thickness. This coating may consist of an electrically or chemically deposited silver coating which is then electrically or chemically treated to form an outer film 124 of silver chloride and an inner layer 126 of silver.

Since the silver-silver chloride layer 122 is only 0.5 to 1.5 mil. in thickness, it could be scratched or chipped during electrode assembly, thereby interrupting the electrical conductive paths formed by this coating. To prevent such interruption, the sensing electrode 106 is provided with dual conductive paths so that a second electrical path is formed through the nonmetallic material 120. This is accomplished by using an electrically conductive nonmetallic material such as an electrically conductive plastic, glass, or glass-plastic combination. For example, a plastic such as ABS plastic, a glass, or a glass-plastic combination, impregnated with carbon within a total content range of from 20–40% by volume or weight has been found to be effective, and a preferred carbon content is 30% carbon by volume or weight.

The sensor element 108 is designed to engage an electrode terminal 128 and to transfer a DC signal thereto. This electrode terminal includes a terminal body 130 having a button connector section 132 projecting outwardly from an annular skirt 134. The button section is round in cross section, and the uppermost portion 136 thereof has a diameter of 0.151 inches or greater and is of a greater cross sectional diameter than the remainder of the button section. As will be noted from FIG. 6, the wall of the upper portion of the button section is of a greater thickness than the wall of the remainder of the button section.

Figure 6:
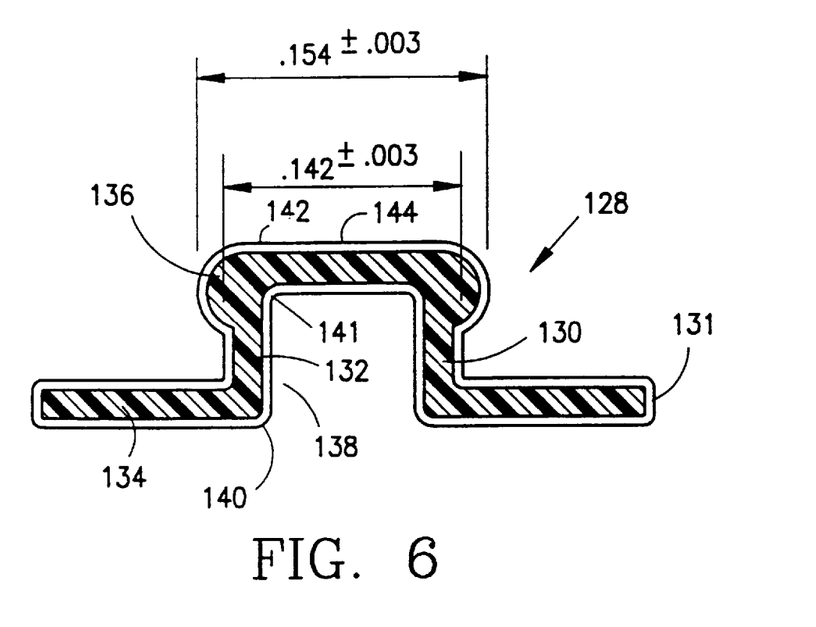
FIG. 6 is a cross sectional view of the terminal for the electrode of FIG. 4.

The body 130 of the electrode terminal includes a central chamber 138 which is dimensioned to receive and tightly grip the mounting pin 114 of the sensor element 108. The edge of the opening into this central chamber is radiused at 140 to prevent surface chipping of the mounting pin as it enters and is forced into the central chamber. Additionally, the edge at the chamber innermost end is radiused at 141 to minimize cracking or chipping of the mounting pin 114 during assembly. The lead and trailing edges of the mounting pin are also radiused as indicated at 123 and 125, respectively. The radiused edges 123 and 141 are formed to conform and are thus radiused the same, while the edges 125 and 140 are also radiused equally but at a greater radius to form a larger arc than is formed at the edges 123 and 141. This provides a wider opening to the chamber 138.

It is important that the outer diameter of the mounting pin 114 conform to the inner diameter of the central chamber 138 within a close tolerance. Thus, with a chamber and pin diameter of 0.086 inches, these diameters should be formed to a tolerance of + or minus 0.001 inches.

Figure 7:
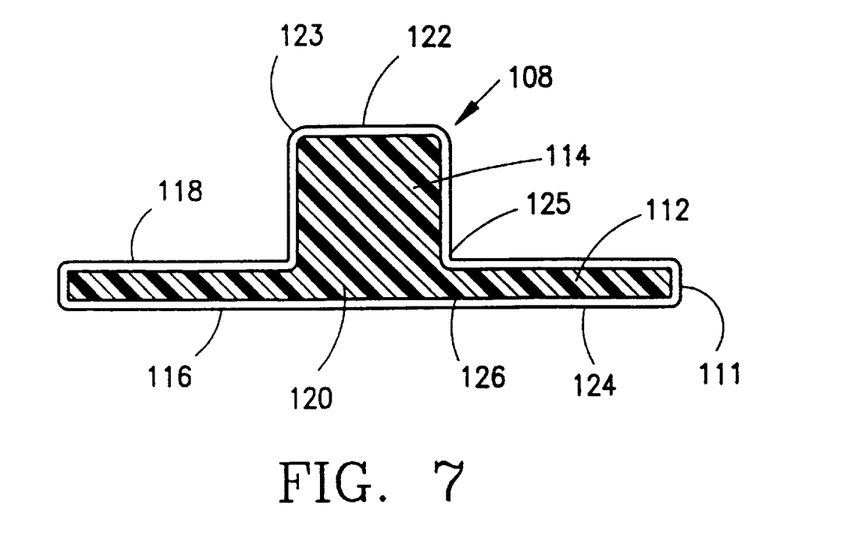
FIG. 7 is a cross sectional view of the sensor for the electrode of FIG. 4.

Like the sensor element 108, the body 130 of the electrode 128 is formed of a nonmetallic material 142, such as plastic, glass or a combination of both coated uniformly with a thin coating 144 of electrically conductive metal. The metal coating on the nonmetallic material 142 must be formed of the same metal used to coat the nonmetallic material 120 of the sensor body 110 to preclude bimetallic support of corrosion within the biopotential sensing electrode 106. Also the thickness of metal coating 144 is preferably 1 mil. but is within a range of from 0.5 to 1.5 mil. When silver is used for the sensor element 108, silver will also be used to coat the electrode terminal 128. Preferably, a second electrical path is formed via the nonmetallic material 142 by using conductive plastic, glass or combination of both for this material. This plastic, glass or glass-plastic combination may be impregnated with carbon and has a carbon content which is preferably 30% but within a range of from 20 to 40% by volume or weight.

To insure that a uniform metal layer is formed on the sensor element body 110 and the electrode body 130, the outer edges 111 and 131, respectively, thereof are not substantially crowned but are radiused so that the metal layer is deposited evenly around each edge. Unradiused edges which provide a sharp edge or corner do not receive a uniform metal layer during electrical or chemical deposition and the metal layer on sharp edges is easily cracked or chipped. By providing relatively thick, radiused edges, the metal flows evenly around the edge during deposition and a uniform metal layer is achieved.

In the formation of the biopotential sensing electrode 106, a sheet of flexible, nonmetallic, liquid impervious barrier material 146 is positioned between the sensor element 108 and the electrode terminal 128 to form a barrier against the passage of liquid. This barrier material has a central opening 148 which permits the mounting pin 114 to pass through the barrier sheet and into the chamber 138 of the electrode terminal. The barrier sheet is adhered and sealed to the second surface 118 of the sensor disc 112 and with the sensor disc forms a primary seal to preclude passage of the electroconductive medium to the electrode terminal 128. When the mounting pin 114 is forced into the chamber 138, the bottom surface of the annular skirt 134 of the electrode terminal is forced into tight contact with the barrier sheet to compress this sheet between the annular skirt and the sensor disc thereby creating a secondary seal between the barrier sheet and the annular skirt. The barrier sheet is preferably formed of a foil material such as polyvinyl chloride.

A circular ring of flexible material 150 is secured and sealed to the barrier sheet 146 and is thicker than the barrier sheet so that a central opening 152 extending therebetween forms a well 154 which contains the electroconductive medium for the DC biopotential sensing electrode 106. This electroconductive medium is in the form of a gel or cream with a high chloride ion content as previously described. The well is positioned relative to the barrier sheet so that the sensor disc 112 is centrally positioned in the well at the end thereof sealed by the barrier sheet. The diameter of the well defines the cross sectional area of a patient's skin which will be contacted by the electroconductive medium, and it should be within a range which is equal to the diameter of the sensor disc to one and one half times the diameter of the sensor disc. To insure that the sensor discs of adjacent electrodes are properly spaced, the outside diameter of the circular ring of flexible material 150 is at least three times the diameter of the sensor disc 112. Thus, if two biopotential sensing electrodes 106 are placed side by side with the edges of the circular rings of flexible material 150 in contact, the distance between the edges of the sensor discs of the two electrodes will be at least twice the diameter of the sensor discs, which is a minimum spacing between discs. If the biopotential sensing electrodes are to provide signals from which a differential value is derived, the sensor discs should be sufficiently spaced so that two adjacent electrodes are not sensing a DC biopotential from the same area of tissue.

The circular ring of flexible material 150 is preferably formed from a flexible foam, such as a cross-linked polyethylene foam, and includes a skin contact surface 156 which is coated with an adhesive acceptable for skin contact. It is this adhesive coated surface which adheres the biopotential sensing electrode 106 to the skin of a subject.

To limit the flow of electroconductive medium 158 from the well 154 and to provide surface tension to maintain the electroconductive medium in contact with the sensor disc 12, a disc 160 of reticulated open cell plastic foam is mounted in the well and is impregnated with the electroconductive medium. This disc 160 extends outwardly from the well beyond the skin contact surface 156, and permits the spread of the electroconductive medium onto the skin of a subject when the biopotential sensing electrode 106 is pressed in place. The open cell plastic foam disc is preferably formed of open cell polyurethene or open cell polyester foam with a cell count which is determined to some extent by the viscosity of the electroconductive medium. Generally the cell count for the plastic foam disc is within a range of from 35–45 cells per square inch.

In use, the disc 160 may be secured to the sheet of barrier material 146 or may be cut to a diameter slightly larger than the diameter of the well 154 so that it is retained in place within the well by tension.

Figure 8:
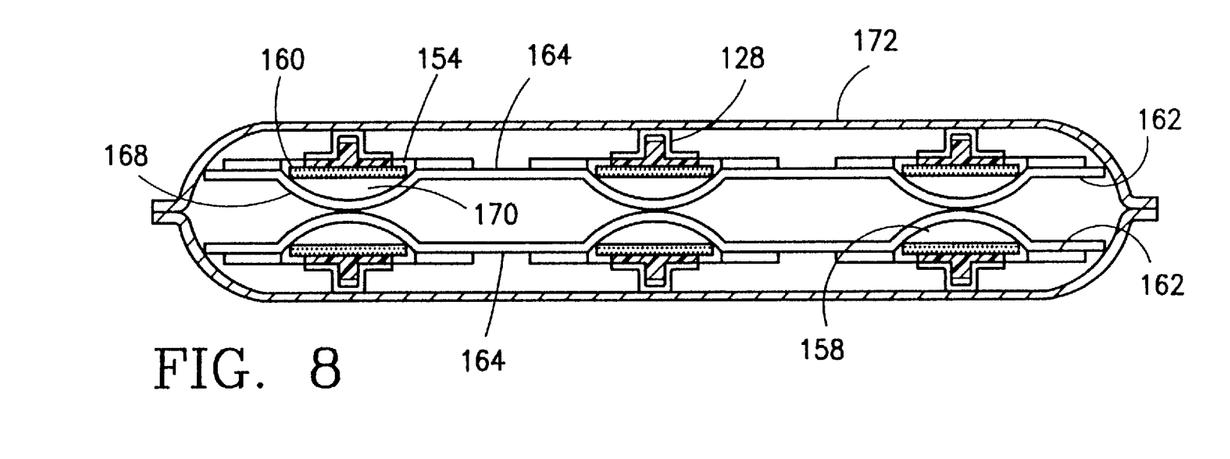
FIG. 8 is a cross sectional view of the packaging unit for the electrode of FIG. 4.
Figure 9:
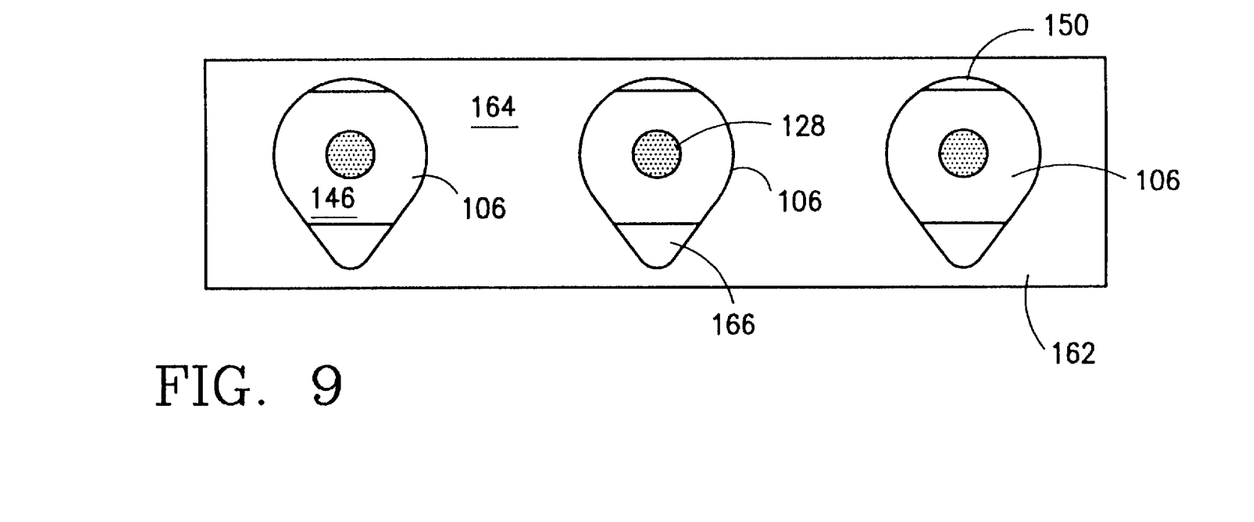
FIG. 9 is a plan view of the electrode of FIG. 4 and the adhesive release strip therefor.

The manner in which the DC biopotential sensing electrodes 106 of the present invention are packaged is quite important, for the high chloride ion content of the electroconductive material 158 causes the water in this material to evaporate rapidly if the electrodes are not properly packaged. Referring now to FIGS. 8 and 9, each electrode 106 is mounted upon a release liner 162 having an upper surface 164 which is an adhesive release surface. The skin contact surface 156 of the electrode 106 is adhered to this adhesive release surface by the adhesive acceptable for skin contact which coats this skin contact surface. To aid in removal of the electrode from the release surface of the release liner 162, the circular ring of flexible material 150 may be provided with a tab section 166, and the skin contact surface of this tab section is not coated with adhesive.

The release liner 162 is formed with a concave depression 168 extending outwardly from the release surface 164 thereof, and this concave depression forms a cavity 170 which opens at the adhesive release surface of the release liner. The diameter of this opening is substantially the same as the diameter of the well 154, and the release liner is positioned so that the well and the opening to the cavity 170 are substantially in alignment. Thus, the cavity 170 contains both the disc 160 of reticulated open cell plastic foam as well as the electroconductive medium which impregnates this disc. The release liner is formed of plastic or of similar fluid and air impervious material, and therefore, seals the electroconductive medium within the well 154 and the cavity 170. The release liner allows the reticulated foam to retain 95% or more of the electroconductive medium and provides a barrier which prevents dehydration of the electroconductive medium while allowing easy removal of the sensor from the release liner. To enable a user to insure that the electroconductive medium has not dried up or leaked away during storage of an electrode 106, the release liner is formed of a clear or transparent material, at least in the area of the concave depression 168, so that the electroconductive material in the cavity 170 and the well 154 may be observed. If visual observation indicates that there is not a sufficient amount of electroconductive material in the cavity 170 and the well 154, the electrode 106 should not be used.

As illustrated in FIGS. 8 and 9, the release liner 162 is preferably formed in strips with a plurality of electrodes 106 mounted upon each strip. To effectively package these electrodes in a manner which insures a long shelf life, two strips of electrodes are placed back-to-back with the concave depressions 168 thereof in contact and with the electrode terminals 128 facing outwardly. It is important that the electrodes be packaged so that the electrode terminals for electrodes in the package are prevented from contacting the electrode terminal of another electrode. The two strips of electrodes are then encased and sealed within a liquid, vapor and gas impervious outer package 172 which is preferably formed of metal foil. The combination of the metal foil outer package and the sealing action provided by the release liner effectively prevents evaporation of the liquid in the electroconductive medium 158.

Industrial Applicability

The DC biopotential sensing electrodes and electroconductive medium of the present invention may be effectively employed with an apparatus for screening or sensing disease states, injury sites or bodily conditions in a living organism by detecting the DC biopotential of the electromagnetic field present between a reference and a plurality of test points on the living organism. These electrodes provide an accurate measurement of the gradient of an electrical activity which occurs as a function of biological activity and yet are designed to resist corrosion and provide an extended shelf life.

We claim:

1. A preassembled biopotential sensing electrode for contact with a skin surface of a human or animal subject and suitable for sensing DC biopotentials which includes an electrode sensing element, an element terminal connected to said electrode sensing element to conduct an electrical potential therefrom, said electrode sensing element being formed from a nonmetallic, electrically conductive material forming a first electrode electrically conductive path, said nonmetallic electrically conductive material being entirely coated with a uniform external coating of an electrically conductive metal, said electrically conductive metal coating forming a second electrode electrically conductive path, said electrode terminal being formed from a nonmetallic, electrically conductive material forming a first terminal electrically conductive path, said nonmetallic electrically conductive material forming said terminal being entirely coated with a uniform external coating of the same conductive metal which coats said electrode sensing element to form a second terminal electrically conductive path, said electrode terminal being connected to said electrode sensing element to conduct an electrical potential therefrom, the conductive metal coating for both said electrode sensing element and said electrode terminal being of a thickness within a range of from 0.5 to 1.5 mil, and and an electroconductive medium for contact with the skin of a subject contacting said electrode sensing element for relaying a biopotential from the skin of a subject to said electrode sensing element, said electroconductive medium having a chloride content within a range of from 6 to 15 g chloride ion per 100 g of electroconductive medium.

2. The biopotential sensing electrode of claim 1 wherein said 6 to 15 g chloride ion includes sodium chloride, potassium chloride and calcium chloride.

3. The biopotential sensing electrode of claim 2 wherein said electrode sensing element and said electrode terminal are electrically conductive and are formed from materials which are corrosion resistant in sodium chloride, potassium chloride and calcium chloride.

4. The biopotential sensing electrode of claim 1 wherein said conductive metal is silver.

5. The biopotential electrode of claim 4 wherein the silver coating on said electrode sensing element includes a uniform layer of silver chloride over a layer of silver.

6. The biopotential sensing electrode of claim 5 wherein said electroconductive medium has a sodium ion content within a range of from 1.4 to 3.2 grams sodium ion per hundred grams of electroconductive medium.

7. The biopotential sensing electrode of claim 6 wherein said electroconductive medium has a potassium ion content within a range of from 1.5 to 7 grams potassium ion content per one hundred grams of electroconductive medium.

8. The biopotential sensing electrode of claim 7 wherein the potassium ion content of said electroconductive medium is equal to or greater than the sodium ion chloride content thereof.

9. The biopotential sensing electrode of claim 1 wherein said electroconductive medium has a pH within a range of 4 to 6.5.

10. An electroconductive medium for a preassembled DC biopotential electrode for contacting the skin of a subject and relaying a D.C. biopotential therefrom to an electrode sensing element comprising chloride in an amount to provide said electroconductive medium with a chloride ion content within a range of from 6 to 15 g chloride ion per 100 g of electroconductive medium, said chloride including sodium chloride, potassium chloride and calcium chloride, a thickener; and water.

11. The electroconductive medium of claim 10 which includes water in an amount equal to 63.4 grams or more per 100 grams of electroconductive medium.

12. The electroconductive medium of claim 11 which includes a paraben preservative.

13. The electroconductive medium of claim 11 in the form of a gel.

14. The electroconductive medium of claim 13 wherein the potassium ion content is equal to or greater than the sodium ion content thereof.

15. The electroconductive medium of claim 14 wherein the potassium ion content is within a range of from 4 to 7 g potassium ion per 100 g of electroconductive medium.

16. The electroconductive medium of claim 15 where said potassium ion content is greater than both said sodium ion content and calcium ion content.

17. The electroconductive medium of claim 16 wherein said thickener includes Hydroxyethyl Cellulose.

18. The electroconductive medium of claim 17 having a pH within a range of 4 to 6.5.

19. The electroconductive medium of claim 11 in the form of a cream.

20. The electroconductive medium of claim 19 wherein the sodium ion content is greater than the potassium ion content.

21. The electroconductive medium of claim 20 wherein said 6–15 g chloride ion includes sodium chloride, potassium chloride and calcium chloride in an amount sufficient to form 7.6–9.06 g chloride per 100 g of cream.

22. The electroconductive medium of claim 20 wherein said thickener includes Propylene Glycol.

23. The electroconductive medium of claim 22 wherein said thickener includes mineral oil.

24. The electroconductive medium of claim 23 which includes a paraben preservative.

25. The electroconductive medium of claim 24 which has a conductivity within a range of from 22,000 to 50,000 micromhos.

26. The electroconductive medium of claim 19 wherein the sodium ion content is within a range of from 2.25 to 3.2 g sodium ion per 100 g of electroconductive medium.

27. The electroconductive medium of claim 26 wherein the potassium ion content is within a range of from 1.5 to 2 g potassium ion per 100 g of electroconductive medium.

28. The electroconductive medium of claim 27 having a conductivity within a range of from 22,000 to 50,000 micromhos.

29. The electroconductive medium of claim 10 having a sodium ion content within a range of from 1.4 to 3.2 g sodium ion per 100 g of electroconductive medium.

30. The electroconductive medium of claim 29 having a potassium ion content within a range of from 1.5 to 7 g potassium ion per 100 g of electroconductive medium.

31. The electroconductive medium of claim 10 having a pH within a range of 4 to 6.5.

32. The electroconductive medium of claim 10 wherein the sodium ion content is greater than the potassium ion content.

33. A preassembled DC biopotential sensing electrode for contact with a skin surface of a human or animal subject comprising:
   an electrode sensing element,
   an electrode terminal connected to said electrode sensing element to conduct an electrical potential therefrom, said electrode sensing element and electrode terminal each being formed from a nonmetallic material completely and uniformly coated with a metallic coating of the same metal, said metallic coating being noncorrosive in sodium chloride, potassium chloride and calcium chloride and of a thickness within a range of from 0.5 to 1.5 mil, and
   an electroconductive medium for contact with the skin surface of said subject contacting said electrode sensing element for transmitting a biopotential from the skin surface to said electrode sensing element, said electroconductive medium having a chloride content within a range of from 6–15 grams per hundred grams of electroconductive medium, said chloride content including sodium chloride, potassium chloride and calcium chloride, the electroconductive medium further including water and a thickener.

34. The D.C. biopotential sensing electrode of claim 33 wherein said electroconductive medium is a gel having a potassium ion content which is equal to or greater than a sodium ion content, the potassium ion content of said gel being within a range of from 4 to 7 g potassium ion per 100 g of electroconductive medium.

35. The D.C. biopotential sensing electrode of claim 34 wherein said thickener includes Hydroxyethyl Cellulose.

36. The D.C. biopotential sensing electrode of claim 35 wherein said electroconductive medium has a pH within a range of 4 to 6.5.

37. The D.C. biopotential sensing electrode of claim 33 wherein said electroconductive medium is a cream having a sodium ion content greater than a potassium ion content.

38. The D.C. biopotential sensing electrode of claim 37 wherein said thickener includes Propylene Glycol.

\* \* \* \* \*